(12) United States Patent
Bertagnoli et al.

(10) Patent No.: US 7,326,216 B2
(45) Date of Patent: Feb. 5, 2008

(54) METHODS AND INSTRUMENTATION FOR POSITIONING IMPLANTS IN SPINAL DISC SPACE IN AN ANTERIOR LATERAL APPROACH

(75) Inventors: Rudolf Bertagnoli, Vienna (AT); Mingyan Liu, Bourg la Reine (FR); Loic Josse, Denens (CH)

(73) Assignee: Warsaw Orthopedic, Inc., Warsaw, IN (US)

( * ) Notice: Subject to any disclaimer, the term of this patent is extended or adjusted under 35 U.S.C. 154(b) by 320 days.

(21) Appl. No.: 10/405,816

(22) Filed: Apr. 2, 2003

(65) Prior Publication Data

US 2004/0199168 A1    Oct. 7, 2004

(51) Int. Cl.
*A61B 17/90* (2006.01)
*A61F 2/46* (2006.01)

(52) U.S. Cl. .................................. 606/90; 606/104
(58) Field of Classification Search .................. 606/90; 623/908
See application file for complete search history.

(56) References Cited

U.S. PATENT DOCUMENTS

| | | | |
|---|---|---|---|
| 4,059,115 A | 11/1977 | Jumashev et al. | |
| 5,772,661 A | 6/1998 | Michelson | |
| 5,860,973 A | 1/1999 | Michelson | |
| 6,200,322 B1 | 3/2001 | Branch et al. | |
| 6,224,603 B1 | 5/2001 | Marino | |
| 6,368,325 B1 | 4/2002 | McKinley et al. | |
| 6,447,512 B1 | 9/2002 | Landry et al. | |
| 6,830,570 B1 * | 12/2004 | Frey et al. | 606/61 |
| 2002/0010473 A1 | 1/2002 | Lin | |
| 2003/0032962 A1 * | 2/2003 | McGahan et al. | 606/80 |

FOREIGN PATENT DOCUMENTS

WO    WO 01/28437 A2    4/2001
WO    WO 01/62166 A2    8/2001

* cited by examiner

*Primary Examiner*—David H. Willse
(74) *Attorney, Agent, or Firm*—Krieg DeVault LLP (57) ABSTRACT

Instruments and methods are provided for positioning one or more implants into a spinal disc space. The instruments and methods have application in an anterior lateral approach to the disc space between the L4 and L5 vertebrae. The instruments include a distractor, a housing, a guide member to facilitate positioning of the housing, and a partition member engageable to the housing to facilitate positioning of one or more implants into the disc space.

28 Claims, 13 Drawing Sheets

METHODS AND INSTRUMENTATION FOR POSITIONING IMPLANTS IN SPINAL DISC SPACE IN AN ANTERIOR LATERAL APPROACH

BACKGROUND

Access to the disc space between the L4 and L5 vertebrae can be obstructed or difficult due to anatomical considerations. For example, an anterior approach or an anterior oblique approach requires the surgeon to retract or move, or at least work adjacent to, the major vessels extending along the anterior portion of the spinal column. While an anterior oblique approach may reduce or eliminate the requirement for retraction of these major vessels, access for positioning instruments and implants in the posterior portion of the disc space on the side of the approach can be limited. Further, the instruments can still be adjacent the major vessels during the surgery.

A lateral approach to the disc space anterior of the posterior elements can avoid the major vessels and provide access for disc space preparation and implant insertion, but other anatomical obstructions can be encountered. For example, positioning instruments and implants in the spinal disc space between the L4 and L5 vertebrae from an anterior lateral approach can be obstructed or inhibited by the iliac crest. Instrumentation and methods which facilitate placement of implants in the spinal disc space from an anterior lateral approach are needed to make such procedures a more viable alternative for treatment and correction of spinal deformities.

SUMMARY

Instruments and methods are provided for positioning one or more implants into a spinal disc space. The instruments and methods have application in an anterior lateral approach to the disc space between the L4 and L5 vertebrae. The instruments and methods can also have application in other approaches to the spine at any level of the spine.

According to one aspect, instruments are provided that include a distractor, a housing, a guide member to facilitate positioning of the housing, and a partition member engageable to the housing to facilitate positioning of one or more implants into the disc space.

According to another aspect, a surgical instrument insertable in a spinal disc space between an upper vertebrae and a lower vertebrae is provided. The instrument comprises a head including an upper surface and an opposite lower surface positionable adjacent endplates of the upper and lower vertebrae, respectively. The head defines a disc space distraction height between the upper and lower surfaces. A shaft extends proximally from the head. The shaft includes a distal portion, a proximal portion, and an offset portion therebetween. The distal portion includes a guide portion adjacent the head. The head and the guide portion extend along a first axis and the offset portion extends proximally from the guide portion along a second axis oriented at a first angle relative to the first axis.

According to a further aspect, a surgical instrument assembly provides access to a spinal disc space. The assembly comprises a distractor, a housing and a guide instrument. The distractor includes a head positionable in a spinal disc space and a shaft extending proximally from the head. The shaft includes a guide portion along at least a portion thereof adjacent the head. The guide instrument includes a shaft and a guide member at a distal end of the shaft. The guide member is removably engaged to the housing and moveable along the guide portion of the distractor with the shaft of the guide instrument adjacent to the shaft of the distractor to guide the housing along the distractor to the spinal disc space when the head is positioned in the spinal disc space.

According to another aspect, an instrument assembly for facilitating placement of an implant in a spinal disc space includes a housing and a partition member. The housing includes a frame member defining an opening therethrough between side walls of the housing. The housing is positionable adjacent to the spinal disc space and provides access thereto through the opening. The partition member is engageable to the frame in the opening. The partition member includes an extension extending distally from the frame and positionable in the spinal disc space. The partition member is movable relative to the frame between the side walls.

According to another aspect, a surgical instrument assembly is provided. The assembly includes a body with a portion positionable in a spinal disc space and a mounting member extending from the body. The assembly also includes a shaft assembly removably engageable to the mounting member. The shaft assembly includes an outer shaft defining a distally opening receptacle and an inner shaft movable relative to the outer shaft and extending distally therefrom. The inner shaft includes a distal engagement member engageable to the mounting member. Movement of the engagement member relative to the outer shaft to position the mounting member in the receptacle secures the body to the shaft assembly.

According to a further aspect, a method for positioning an implant in a spinal disc space of a patient comprises: accessing the spinal disc space between L4 and L5 vertebrae from a lateral approach to the patient; and positioning a distractor in the spinal disc space with a shaft of the distractor oriented laterally to the patient, the shaft comprising a distal portion extending laterally from the spinal disc space and a proximal portion offset relative to the distal portion anteriorly of the iliac crest.

According to another aspect, a method for positioning a spinal implant in a spinal disc space of a patient comprises: positioning a housing adjacent the disc space between the L4 and L5 vertebrae in an anterior lateral approach; positioning a partition member through the housing into the disc space; positioning an implant in the disc space anterior of the partition member; and moving the partition member anteriorly to move the implant anteriorly in the spinal disc space.

These and other aspects are also discussed below.

DESCRIPTION OF THE ILLUSTRATED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
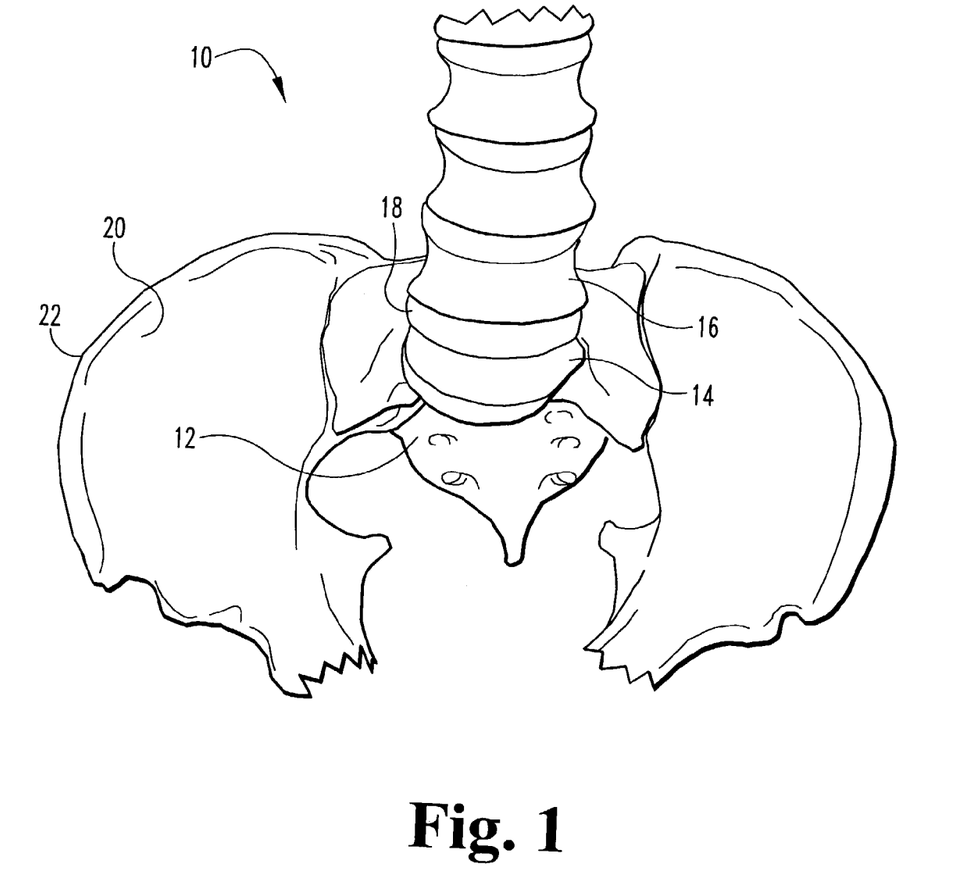
FIG. 1 is an anterior elevation view of a sacro-lumbar segment of the spinal column.

Referring to FIG. 1, there is shown a spinal column segment 10 that includes a sacrum 12, an L5 vertebrae 14, an L4 vertebrae 16, and a disc space 18 between L5 vertebrae 14 and L4 vertebrae 16. The present invention provides methods and instrumentation adapted for positioning spinal implants in disc space 18 from an anterior lateral approach that avoid or minimize the obstruction of iliac crest 20 into an access pathway to disc space 18. The instruments and methods provide anterior lateral access to the disc space for endplate preparation and implant insertion into disc space 18 to support of the adjacent vertebrae with one or more medial-laterally oriented implants.

In surgical procedures for accessing disc space 18, it can be desirable to approach disc space 18 from a lateral approach along the anterior side of iliac crest 20. With such an anterior lateral approach, the major arteries and veins along the anterior portion of the spine can be avoided. Furthermore, the posterior neural elements, musculature, and bony structures can be avoided. With the anterior lateral approach, one or more implants can be positioned in disc space 18 in such a manner that the load of the spinal column transmitted by the implants is evenly distributed about the central axis of the spinal column. However, iliac crest 20, particularly along its outer margin 22, can extend anteriorly relative to disc space 18 such that anterior lateral access to disc space 18 is impeded thereby.

Figure 2:
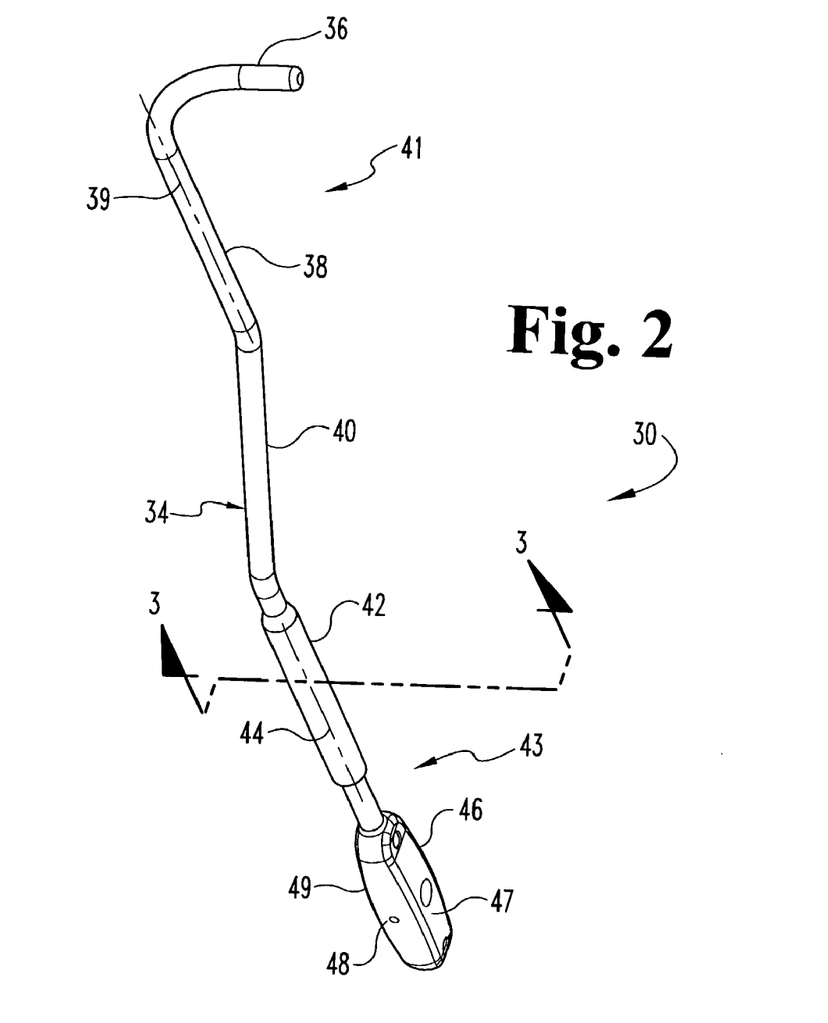
FIG. 2 is a perspective view of a disc space distractor.

Referring now to FIG. 2, there is shown a disc space distractor 30 including a distal head 32 and a shaft 34 extending proximally therefrom. Head 32 can include a first vertebral endplate surface 46 and an opposite second vertebral endplate surface 48. First and second side surfaces 47, 49 extend between first and second vertebral endplate surfaces 46, 48. First and second vertebral endplate surfaces 46, 48 can be spaced from one another to contact the adjacent vertebral endplates, or to provide a desired disc space height between the vertebral endplates when head 32 is inserted into disc space 18 with first and second vertebral endplate surfaces 46, 48 adjacent respective ones of the vertebral endplates. It is contemplated that distractor 30 could be any one of a number of distractors provided in a kit in which the distractors have heads of differing heights so that the distractor corresponding to or providing the proper disc space height can be selected. It is further contemplated that head 32 can be non-distracting, and is positioned in the disc space to facilitate positioning of instruments in the desired operative location relative to disc space 18, as discussed below.

Shaft 34 includes a proximal portion 41 and a distal portion 43 separated by an offset portion 40. Proximal portion 41 includes a first shaft portion 38 extending proximally from offset portion 40 along an axis 39. A handle 36 extends from first shaft portion 38 and is oriented transversely to axis 39. Distal portion 43 includes a guide portion 42 extending distally from offset portion 40 along an axis 44. Head 32 extends distally from guide portion 42. As discussed further below, guide portion 42 can be adapted to guide placement of a housing therealong to a position adjacent disc space 18 when head 32 is positioned in the disc space.

Figure 3:
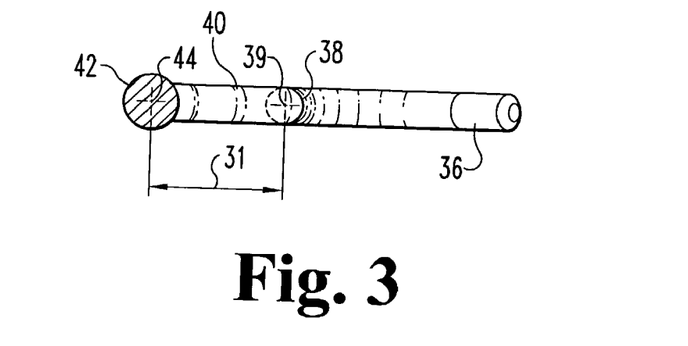
FIG. 3 is a section view of the distractor of FIG. 2 along line 3—3.

As shown further in FIG. 3, offset portion 40 is angled to position proximal portion 41 anteriorly of distal portion 43 when distractor 30 is operatively positioned in an anterior lateral approach to the disc space. Distal portion 43 can thus be positioned in the disc space posteriorly to avoid the major vessel and other structures along the anterior portion of the spinal column segment. Longitudinal axis 39 is offset anteriorly by a distance 31 from longitudinal axis 44. It is contemplated that offset distance 31 is sufficient so that with head 32 positioned in the spinal disc in its operative anterior lateral orientation, distal portion 43 extends along longitudinal axis 44 from the disc space and proximal portion 41 is offset anteriorly to avoid the iliac crest. In the operative position, handle 36 extends anteriorly to provide additional room for access and placement of surgical instruments along the posterior side of distractor 30.

In one embodiment, offset portion 40 is spaced proximally about 60 millimeters from the trailing end of distraction head 32, and offset distance 31 is about 20 millimeters. Other suitable dimensions and offsets are also contemplated so that proximal portion avoids the iliac crest when distractor 30 is inserted in an anterior-lateral approach to the disc space.

Figure 4:
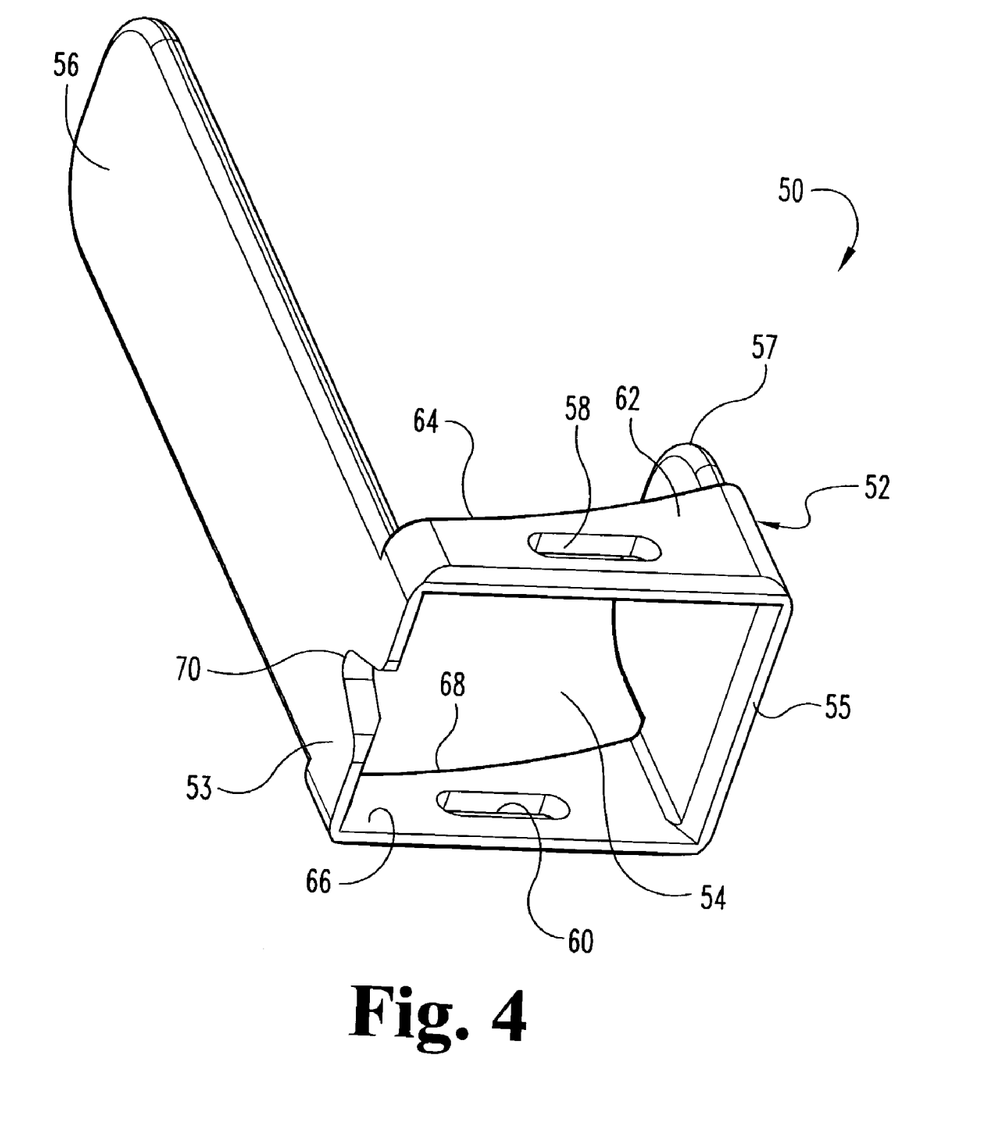
FIG. 4 is a perspective view of a housing.

In FIG. 4 there is shown a housing 50 comprising a frame portion 52 including a posterior side wall 53 and an anterior side wall 55 connected by an upper wall 62 and a lower wall 66. Walls 53, 55, 62, 66 define an opening 54 through which in the operative position of housing 50 instruments and implants can be inserted into the spinal disc space. Opening 54 is shown with a rectangular shape. Also contemplated is a square shape or other suitable shape. Frame portion 52 includes a posterior extension 56 extending from posterior side wall 53 and an anterior extension 57 extending from anterior side wall 55. Posterior extension 56 can be provided with a length greater than that of anterior extension 57 such that posterior extension 56 extends substantially across disc space 18 to protect the posterior portion of the spinal column from intrusion by surgical instruments and implants during the surgical procedure and to maintain disc space distraction. Anterior extension 57 has a length sufficient to extend into the disc space to contact the cortical rim to assist posterior extension 56 in maintaining spacing of the adjacent vertebrae during the surgical procedure. It is further contemplated that the length of anterior extension 57 does not extend into the implant insertion location in the anterior portion of the disc space and, as discussed further below, allows a spinal implant to be positioned at least in part anteriorly thereof. Other embodiments contemplate an anterior extension 57 that extends across all or part of the disc space.

Upper wall 64 of frame portion 52 includes an upper slot 58 formed therethrough and lower wall 66 includes a lower slot 60 formed therethrough. Slots 58, 60 facilitate coupling of housing 50 to an instrument, such as shaft assembly 126 discussed further below, so that the shaft assembly can remove housing 50 from the disc space. Upper wall 62 includes a leading end 64 curved to conform to the curvature of the vertebral body against which it is positioned in the operative position of housing 50. Similarly, lower wall 66 includes a leading end 68 curved to conform to the curvature of the vertebral body against which it is positioned in the operative position of housing 50. A proximally-opening notch 70 is provided in posterior wall 53.

Figures 5, 6:
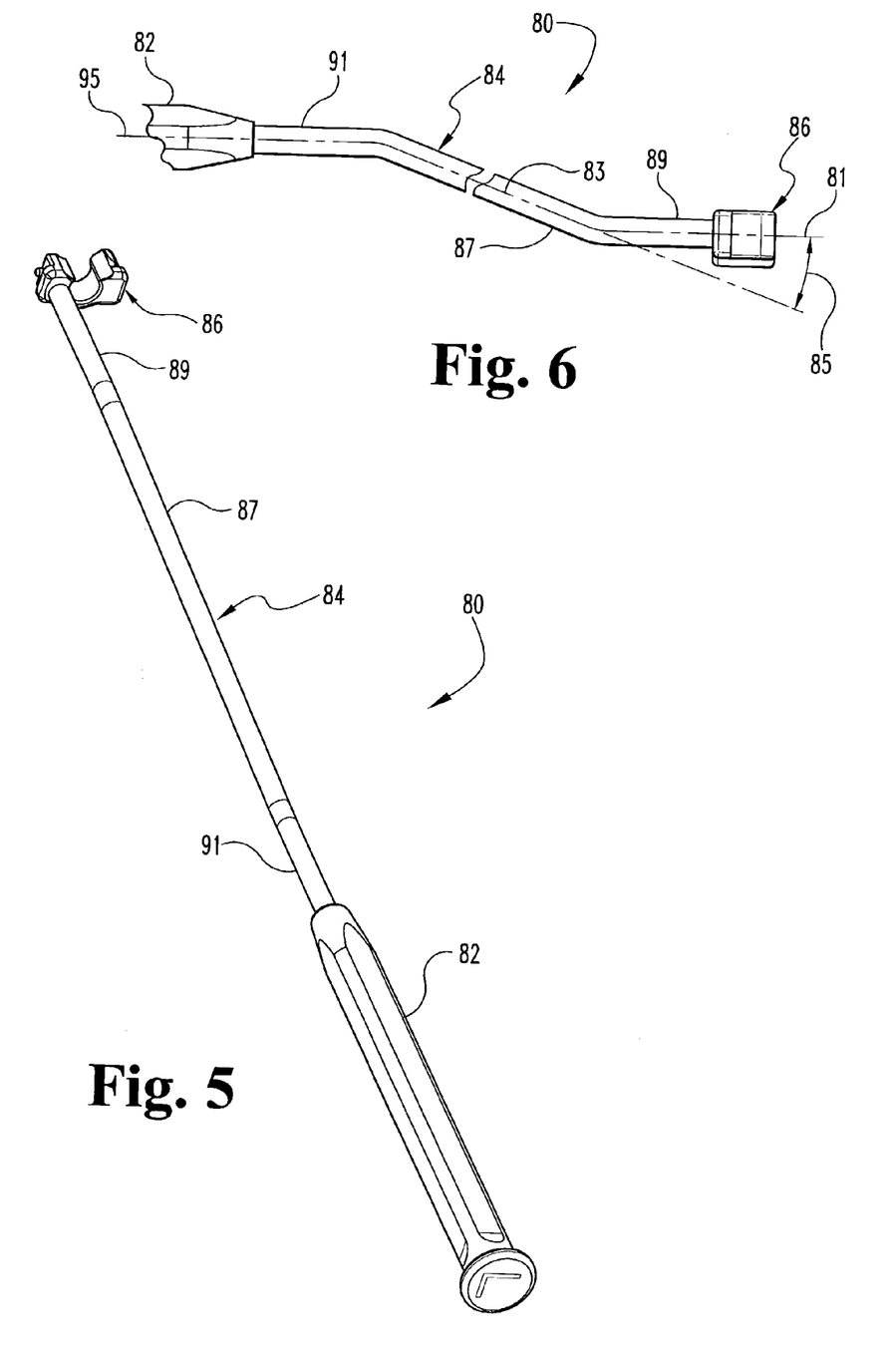
FIG. 5 is a perspective view of a guide instrument attachable to the housing of FIG. 4.
FIG. 6 is an elevation view of a portion of the guide instrument of FIG. 5.

In FIGS. 5 and 6 there is shown a guide instrument 80 in perspective and side elevational views, respectively. Guide instrument 80 includes a proximal handle 82, a shaft 84 extending distally from handle 82, and a guide member 86 at the distal end of shaft 84. Guide member 86 includes a passage 90. Shaft 84 includes a distal portion 89, a proximal portion 91, and an offset portion 87 therebetween. Distal portion 89 extends along an axis 81, offset portion 87 extends along an axis 83, and proximal portion 91 extends along an axis 95. Axis 95 and axis 81 can be generally parallel to one another. Axis 83 forms an angle 85 with axis 81 and axis 95.

Figure 7:
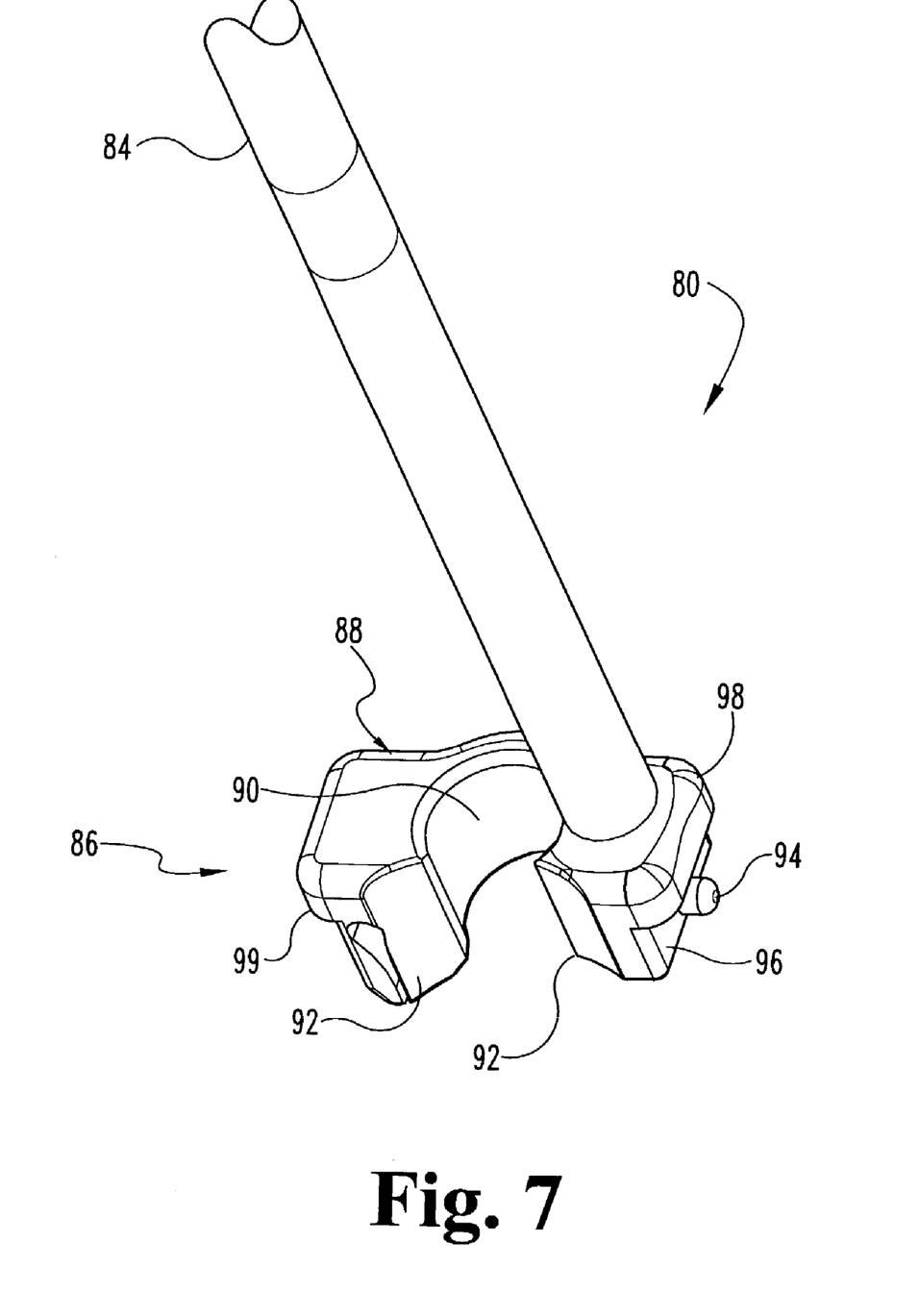
FIG. 7 is an enlarged perspective view of a guide member at the distal end of the guide instrument of FIG. 5.

As shown in further detail in FIG. 7, distal portion 89 is offset from passage 90 so that distal portion 89 of shaft 84 can extend adjacent to guide portion 42 of shaft 34 of distractor 30 as guide member 86 is moved along guide portion 42. In the illustrated embodiment, distal portion 89 is offset posteriorly from passage 90 in the operative anterior lateral orientation so that shaft 84 extends along the posterior side of shaft 34 of distractor 30 in side-by-side relation. As guide instrument 80 is inserted to the disc space in an anterior lateral approach, angle 85 offsets proximal portion 91 cephaladly to avoid the iliac crest. Offset portion 87 can be further configured relative to distal portion 89 to offset proximal portion 91 anteriorly by a distance 31, such as discussed above with respect to distractor 30. In one embodiment, angle 85 is about 30 degrees. Other embodiments contemplated angles 85 up to 90 degrees so long as proximal portion 91 avoids the iliac crest when positioned in an anterior lateral approach.

Guide member 86 includes a body 88 defining guide passage 90 extending between a distal end and a proximal end of body 88. Tapered surfaces 92 provide an opening into passage 90 along one side of body 88. Guide passage 90 is sized to receive guide portion 42 of distractor 30 therein in close-fitting and sliding engagement to permit controlled relative movement of guide member 86 along guide portion 42. Body 88 includes a distal portion 96 and a proximal portion 98. Proximal portion 98 includes a flanged wall 99 extending about and forming a lip about distal portion 96. Distal portion 96 is sized for positioning in opening 54 of housing 50 with flanged wall 99 in abutting engagement with the proximal end of housing 50.

Figure 8:
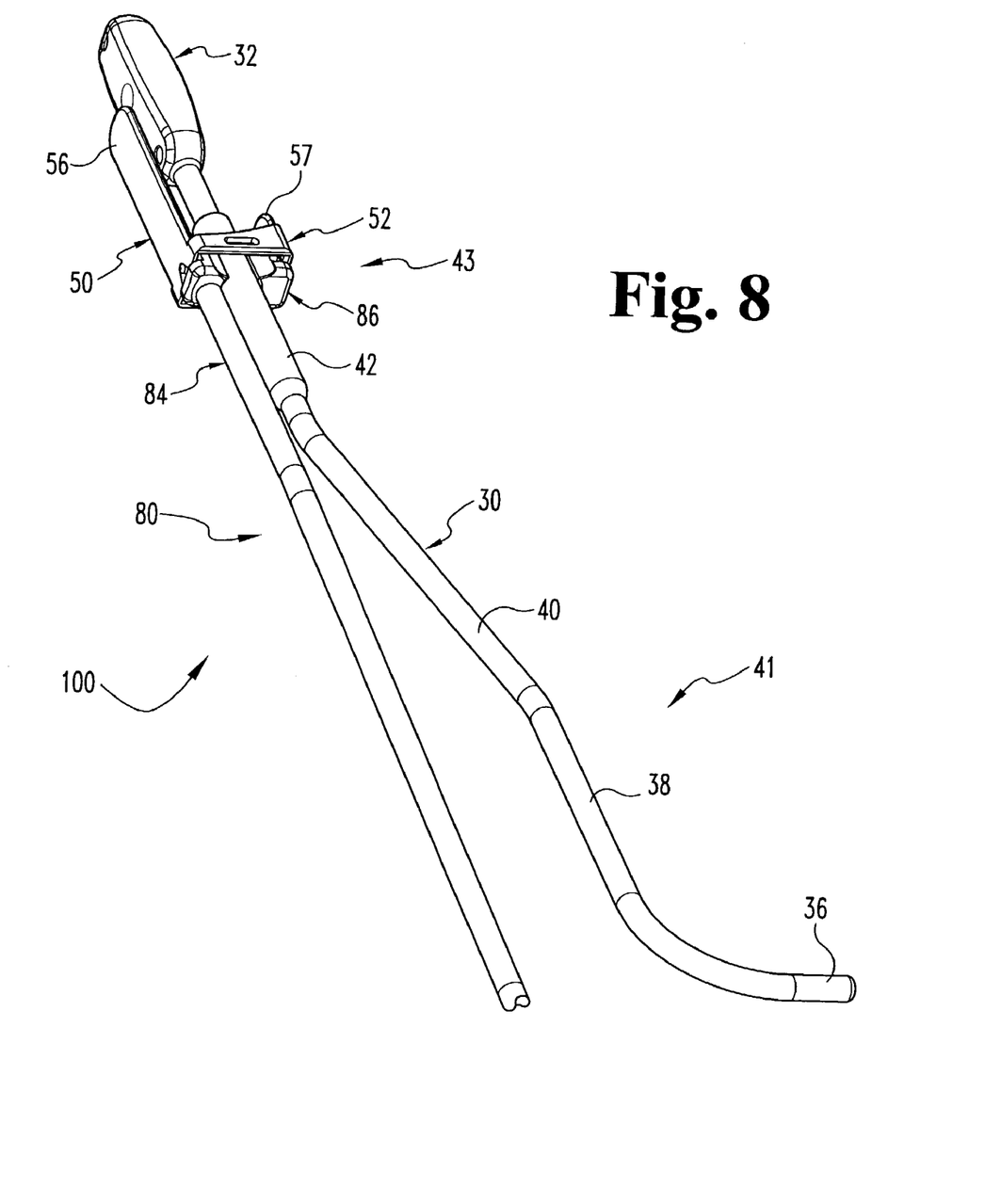
FIG. 8 is a perspective view of a housing insertion instrument assembly comprising the distractor of FIG. 3, the housing of FIG. 4 and the guide instrument of FIG. 5.

In FIG. 8, a housing insertion instrument assembly 100 is provided that includes distractor 30, housing 50 and guide instrument 80. Guide member 86 is positioned in opening 54 of housing 50 with protrusion 94 received in receptacle 70 and flanged wall 99 in abutting engagement with the proximal end of housing 50. With distractor 50 positioned in the desired position in disc space 18, offset portion 40 is configured so that proximal portion 41 is positioned away from the iliac crest to provide space to receive guide instrument 80 and housing 50 therebetween.

Shaft 34 of distractor 30 is positioned in passage 90 of guide member 86 proximal of guide portion 42. Guide member 86 and housing 50 are advanced to position guide portion 42 in passage 90. Guide portion 42 can have a cross-section enlarged relative to the proximal portion of shaft 34 for sliding engagement with passage 90. It is contemplated that passage 90 of guide member 86 can be keyed to guide portion 42 to prevent rotation of guide instrument 80 thereabout and to ensure the proper orientation of housing 50 as it is guided to the disc space. Circular cross-sections are also contemplated. Housing 50 is guided along guide portion 42 to position frame 52 adjacent the L4 and L5 vertebrae, and to position posterior extension 56 and anterior extension 57 in the disc space. With housing 50 in its proper position relative to disc space 18, distractor 30 and guide instrument 80 are removed proximally from housing 50 with housing 50 remaining at the operative site. Opening 54 of housing 50 provides access to the disc space for removal of disc material, endplate preparation and implant insertion. It is also contemplated that disc material removal, endplate preparation and other pre-implant insertion procedures can be conducted prior to positioning of housing 50.

Figure 9:
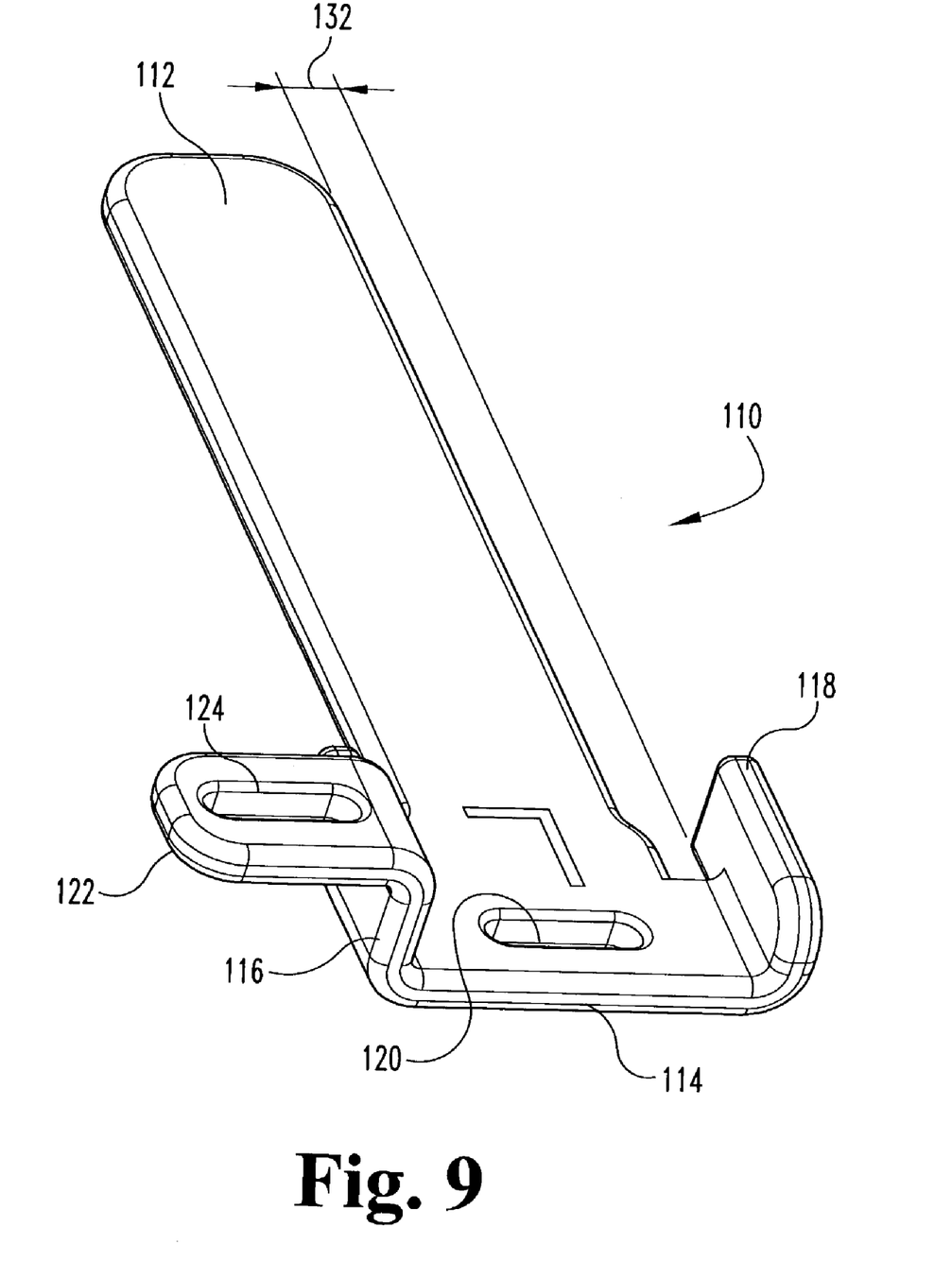
FIG. 9 is a perspective view of a partition member.

Referring to FIG. 9, there is shown a partition member 110 having a body 114 and a central extension 112 extending distally from body 114. Body 114 includes an upper flange member 116 and a lower flange member 118 extending from and transversely oriented to body 114. A mounting member 122 extends transversely to and, in the operative anterior lateral orientation, cephaladly from upper flange member 116. Mounting member 122 includes a slot 124 to facilitate attachment to an insertion instrument. A slot 120 in body 114 is provided for engagement by a shaft assembly to facilitate withdrawal and manipulation of partition member 110 relative to housing 50.

Figures 10, 11:
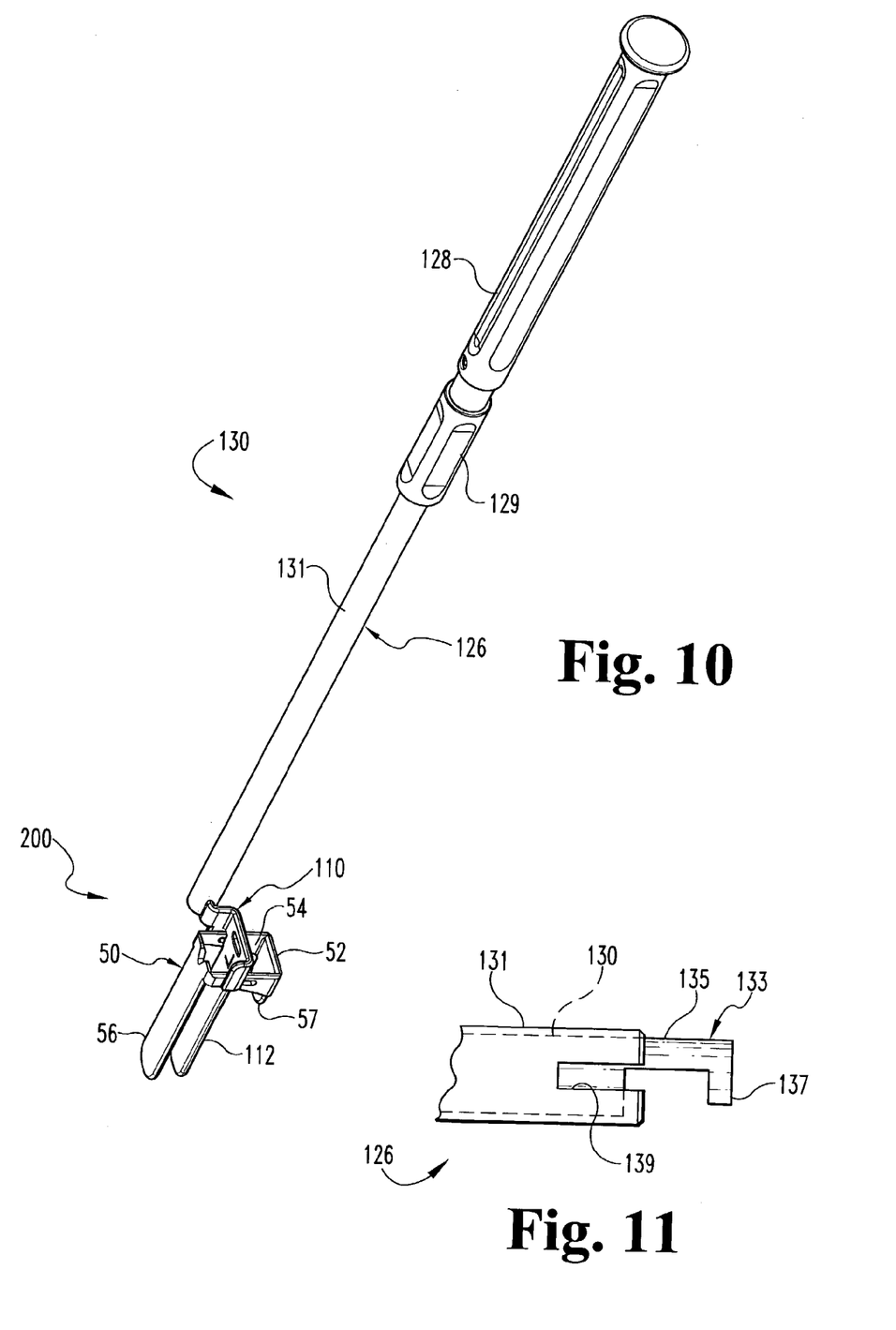
FIG. 10 is a perspective view of an implant insertion instrument assembly comprising the housing of FIG. 4 and the partition member of FIG. 9.
FIG. 11 is an elevation view of a shaft assembly comprising a portion of the implant insertion instrument assembly.

In FIG. 10 there is shown an implant insertion instrument assembly 200 including housing 50 and partition member 110. Partition member 110 is removably mounted to the distal end of a shaft 126 assembly. A proximal handle 128 is provided at the proximal end of an inner shaft 130, and a distal handle 129 is coupled to an outer shaft 131. As shown in FIG. 11, the distal end of inner shaft 130 can include an engagement member 133 that includes a distal extension 135 and a hook member 137 extending from and transversely oriented to distal extension 135. Hook member 137 can be positioned in slot 124 of mounting member 122, and outer shaft 131 can be moved distally relative to inner shaft 130 to secure mounting member 122 in a distally opening receptacle in outer shaft 131 such as slot 139. It is contemplated that outer shaft 131 can be threadingly coupled to inner shaft 130, or that outer shaft 131 can be spring-biased distally relative to inner shaft 130. Movement of outer shaft 131 and inner shaft 130 relative to one another can remove mounting member 122 from slot 139 and allow hook member 137 to be withdrawn from slot 124 of mounting member 122.

Partition member 110 can be attached to shaft assembly 126 and positioned through opening 54 of housing 50 so that central extension 112 extends into the disc space between posterior extension 56 and anterior extension 57. When inserted through opening 54 of housing 50, upper flange member 116 is positioned along upper wall 62, and lower flange member 118 is positioned along lower wall 66. Mounting member 122 extends upwardly from upper wall 62 so that shaft assembly 126 is located above the iliac crest at its proximal end when secured to mounting member 122. Spacing 132 between the flange members 116, 118 and body 114 can be provided to receive the thickness of the upper and lower walls 62, 66 for sliding engagement therewith as partition member 110 is moved relative to housing 50. Upper and lower walls 62, 66 can be parallel to one another to facilitate the sliding movement of partition member 100 therealong.

Figure 12:
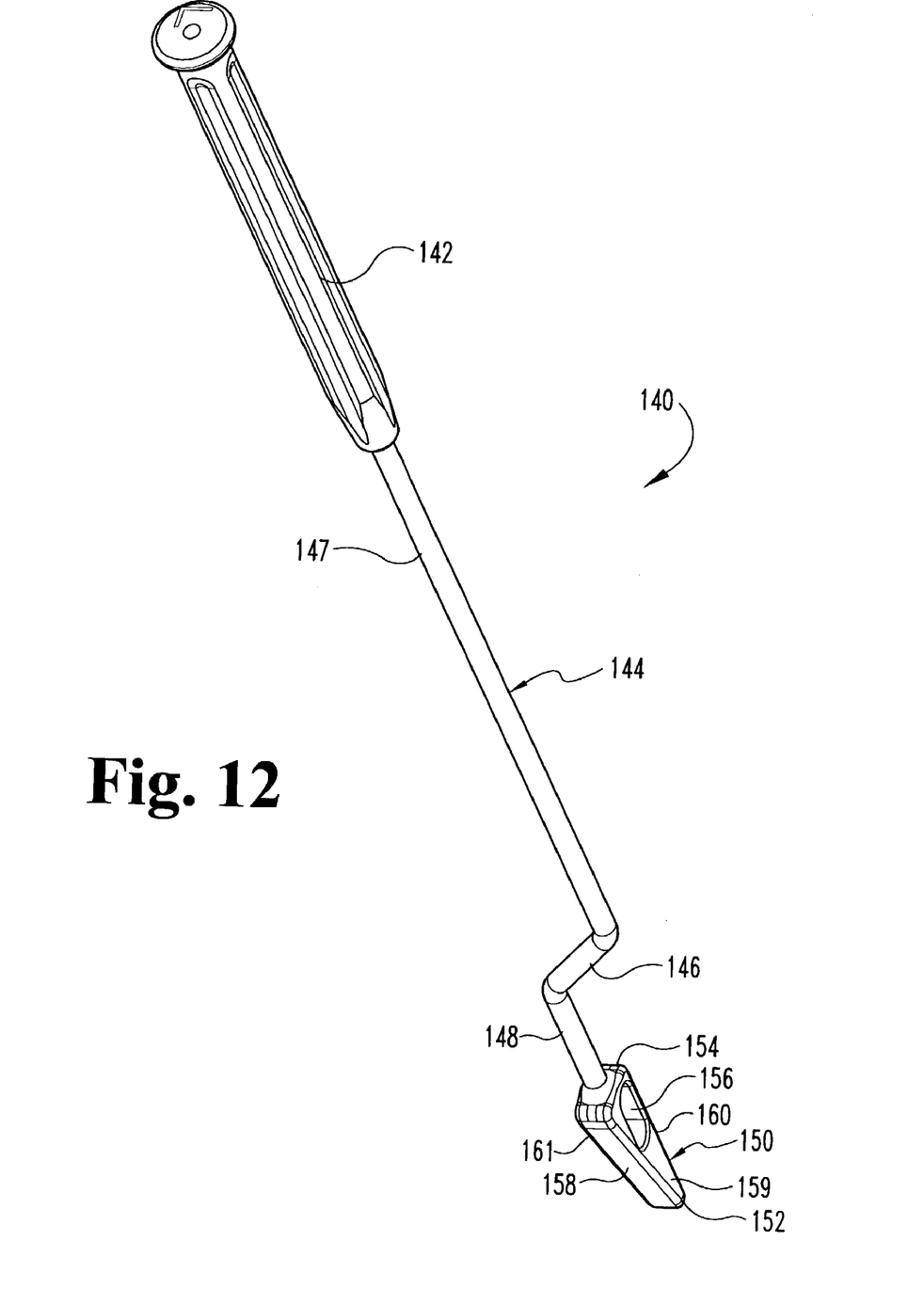
FIG. 12 is a perspective view of a wedge displacer instrument.

In FIG. 12 there is shown a wedge displacer instrument 140 comprising a handle 142 and a shaft 144 extending distally from handle 142. Shaft 144 includes an offset portion 146 separating shaft 144 into a proximal portion 147 and a distal portion 148. Distal portion 148 can extend generally parallel to proximal portion 147. A displacer wedge 150 extends distally from distal portion 148 of shaft 144. Displacer wedge 150 includes a lead end 152 and a trailing end 154. A first lateral surface 158 and a second lateral surface 160 extend from leading end 152 to trailing end 154 between a first surface 159 and an opposite second surface 161. Surfaces 158, 160 and ends 152, 154 form a wedge shape such that leading end 152 has a reduced width relative to trailing end 154. The reduced width leading end 152 facilitates insertion of displacer wedge 150 between posterior extension 56 of housing 50 and partition member 110. A bore 156 can be formed between first and second surfaces 159, 161 of displacer wedge 150 to reduce the weight of displacer wedge 150, although a solid displacer wedge 150 is also contemplated.

Figure 13:
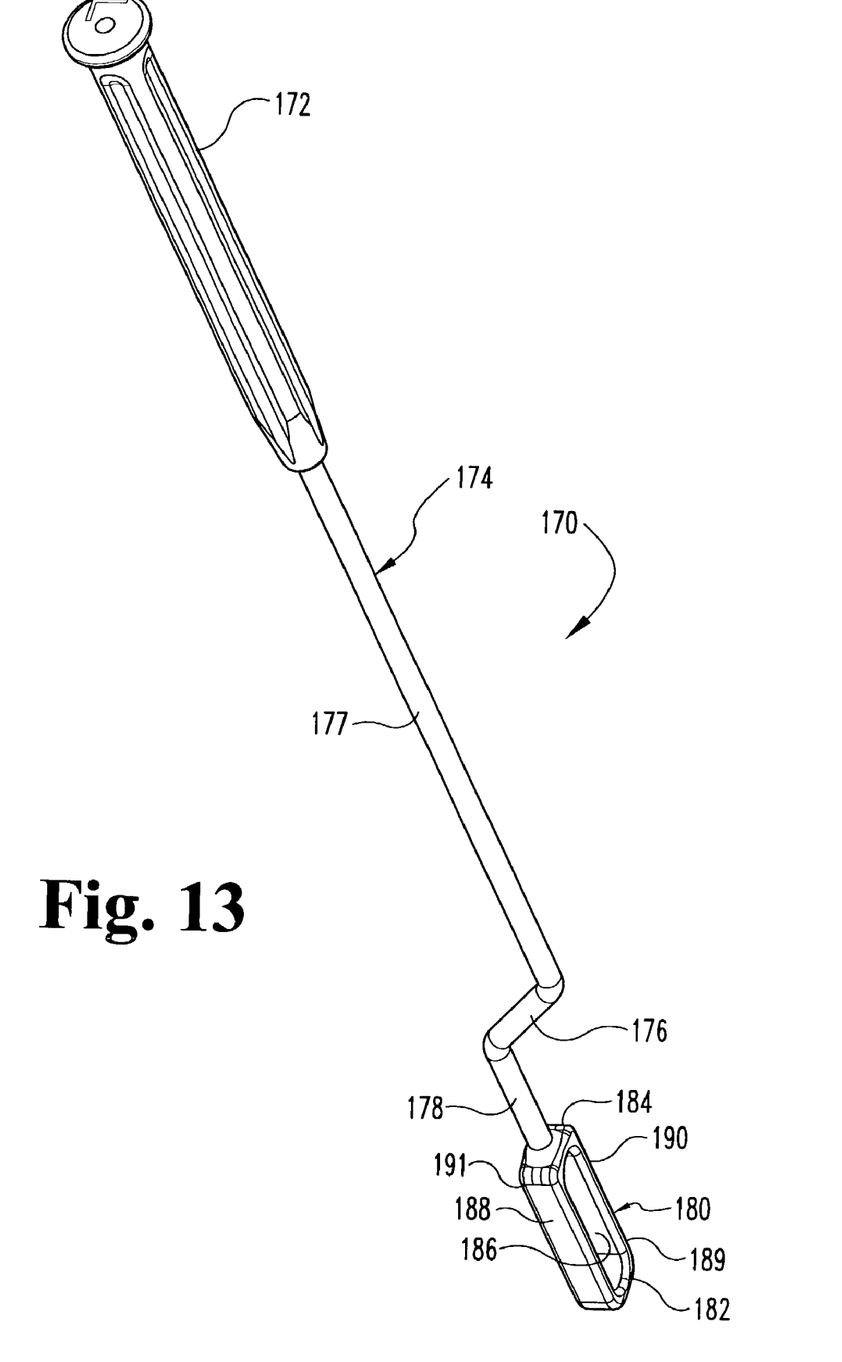
FIG. 13 is a perspective view of a second displacer instrument.

In FIG. 13 there is shown a second displacer instrument 170 comprising a handle 172 and a shaft 174 extending distally from handle 172. Shaft 174 includes an offset portion 176 separating shaft 174 into a proximal portion 177 and a distal portion 178. Distal portion 178 can extend generally parallel to proximal portion 176. A displacer head 180 extends distally from distal portion 178 of shaft 174. Displacer head 80 includes a lead end 182 and a trailing end 184. A first lateral surface 188 and a second lateral surface 190 extend from leading end 182 to trailing end 184 between a first surface 189 and an opposite second surface 191. Surfaces 188, 190 and ends 182, 184 form a box shape such that leading end 182 has the same width as trailing end 184. Other shapes are also contemplated so long as leading end 182 provides the desired displacement of the implant at the distal end of partition member 110. A bore 186 is formed between first and second surfaces 189, 191 of displacer head 180 to reduce the weight of displacer head 180, although a solid displacer head 180 is also contemplated.

In use, displacer wedge 150 of wedge displacer instrument wedge 140 can be been inserted between partition member 110 and posterior extension 56 of housing 50 to provide an initial separation. With wedge displacer instrument 140 removed, second displacer instrument 170 is positioned with leading end 182 of displacer head 180 between posterior extension 56 of housing 50 and partition member 110. Leading end 182 can provide a separation between the distal ends of posterior extension 56 and partition member 110 that corresponds to the width of leading end 182.

Figure 14:
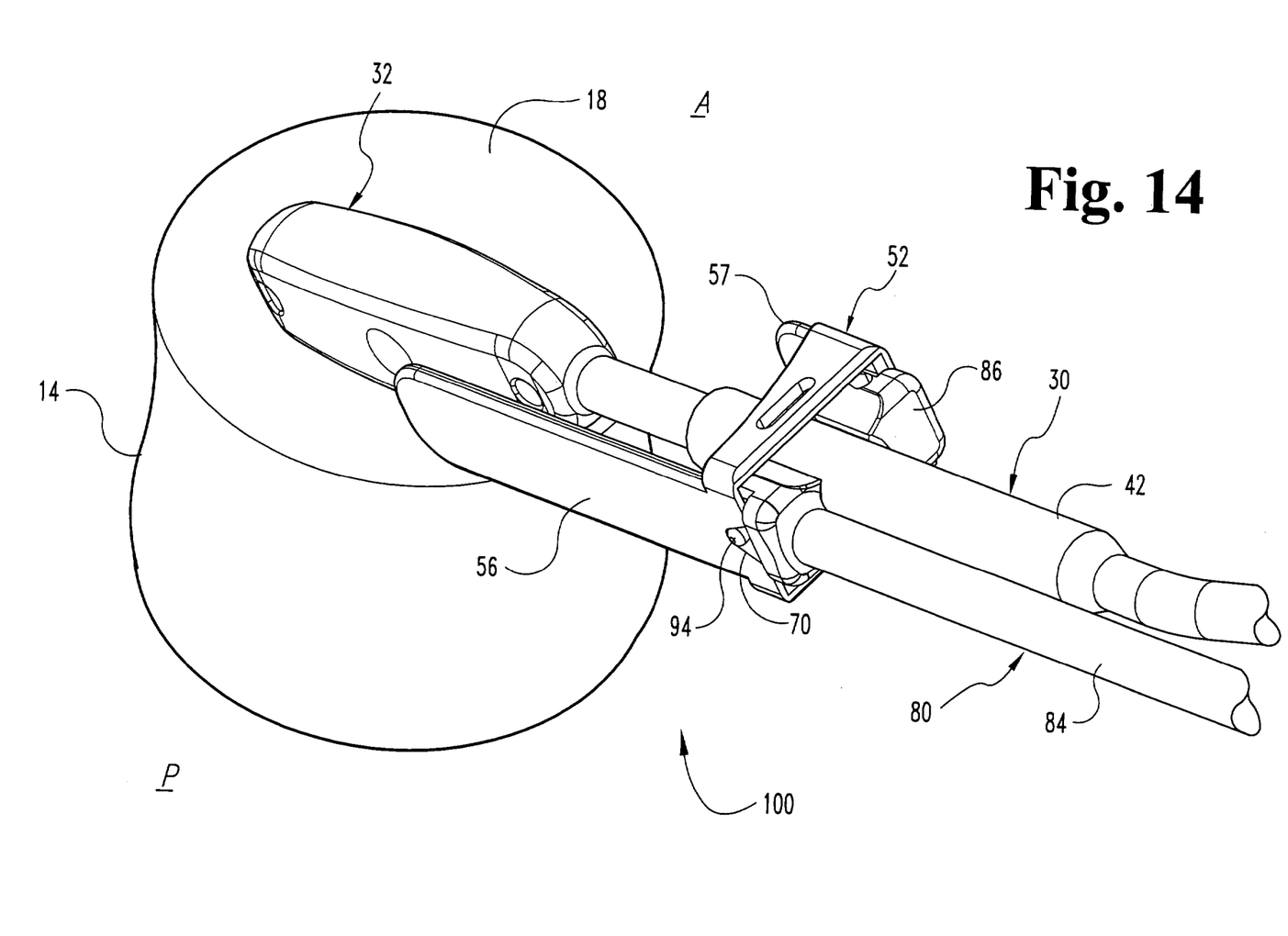
FIG. 14 is perspective view looking down on the distal end portion of the assembly of FIG. 8 positioned adjacent a lower vertebrae of a spinal column segment with the distractor in the spinal disc space and the housing being positioned with the guide instrument to provide access to the spinal disc space.

With reference to FIGS. 14–19, a surgical procedure will be described for positioning a pair of interbody implants in spinal disc space 18 through an anterior lateral approach with the instruments discussed above. In FIG. 14 housing insertion instrument assembly 100 includes distractor 30 with distractor head 32 positioned at the desired location in disc space 18. The location of head 32 can be confirmed with fluoroscopy or other suitable viewing system. It is contemplated that head 32 will be located centrally in disc space 18 and extend in the medial-lateral direction in its final orientation, although other final orientations are contemplated. Shaft 34 of distractor 30 extends from disc space 18 laterally, and shaft 34 is offset anteriorly to avoid the iliac crest, as discussed above.

Housing 50 is mounted to guide member 86 of guide instrument 80 and then positioned about shaft 34 of distractor 30. Guide member 86 and thus housing 50 are guided along guide portion 42 to position posterior extension 56 laterally along the posterior portion P of disc space 18 and anterior extension 57 laterally along the anterior portion A of disc space 18. Frame 52 is positioned adjacent the vertebrae 14, 16 outside disc space 18 so that opening 54 can provide access to disc space 18 while extensions 56, 57 maintain disc space distraction.

Figure 15:
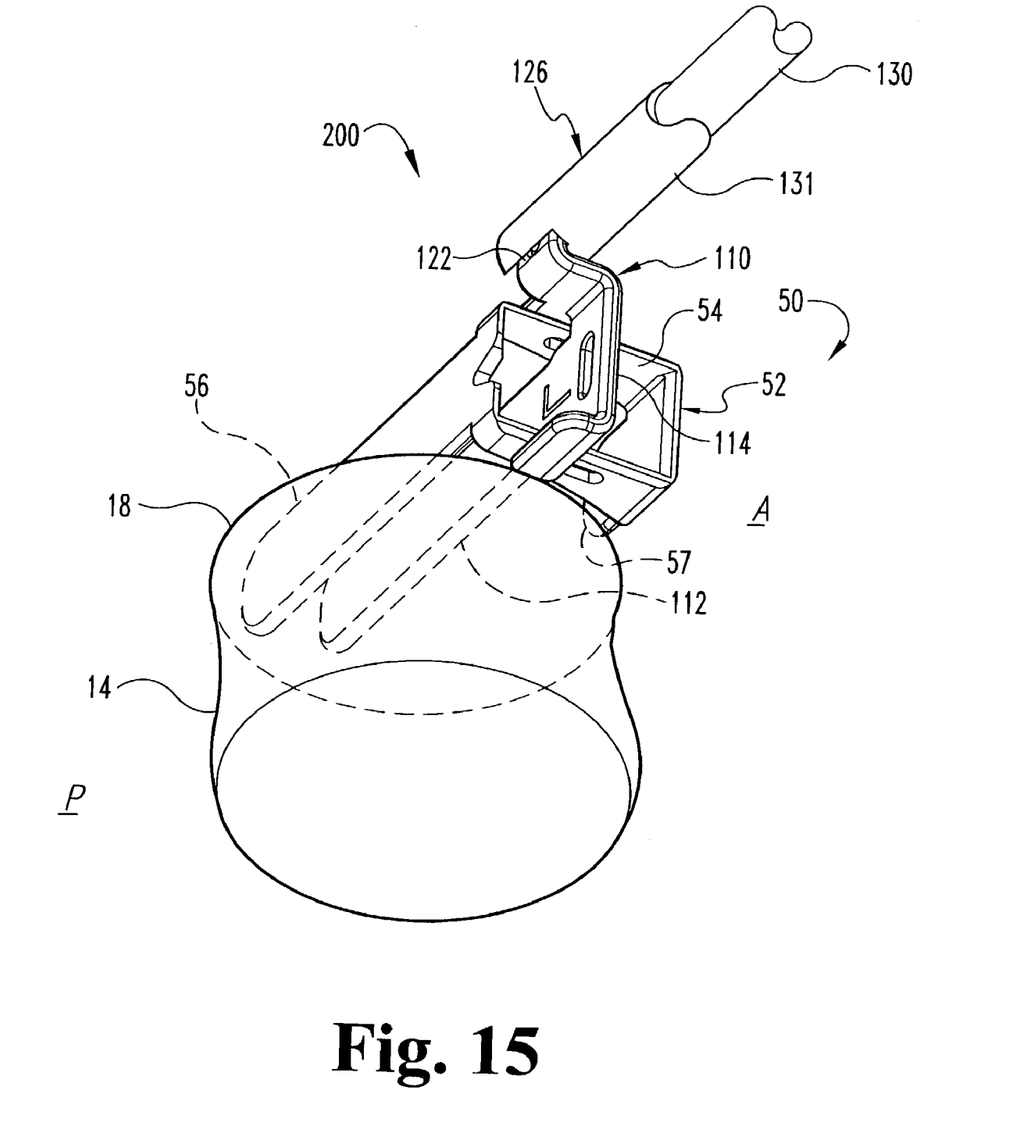
FIG. 15 is a perspective view of the distal end portion of the assembly of FIG. 10 looking up through the endplate of the lower vertebrae of FIG. 14.

Referring now to FIG. 15, distractor 30 and guide instrument 80 are removed from housing 50. Mounting member 122 of partition member 110 is attached to shaft assembly 126. Since mounting member 122 extends cephaladly from housing 50, shaft assembly 126 is positioned cephaladly of the iliac crest as partition member 110 is inserted through opening 54 of housing 50. Shaft assembly 126 is manipulated to position partition member 110 through opening 54 of housing 50 so that central extension 112 extends into the disc space between posterior extension 56 and anterior extension 57. Body 114 of partition member 110 is received in frame portion 52 with upper flange 116 and lower flange 118 positioned along upper wall 62 and lower wall 66, respectively, to guide partition 110 as it is moved relative to housing 50. Partition member 10 is positioned as close as possible to posterior extension 56 to maximize the space anteriorly of partition member 110 through opening 54 for positioning of an implant therethrough. With partition member 110 secured in housing 50, shaft assembly 126 can be uncoupled from partition member 110.

Figures 16, 17, 18, 19:
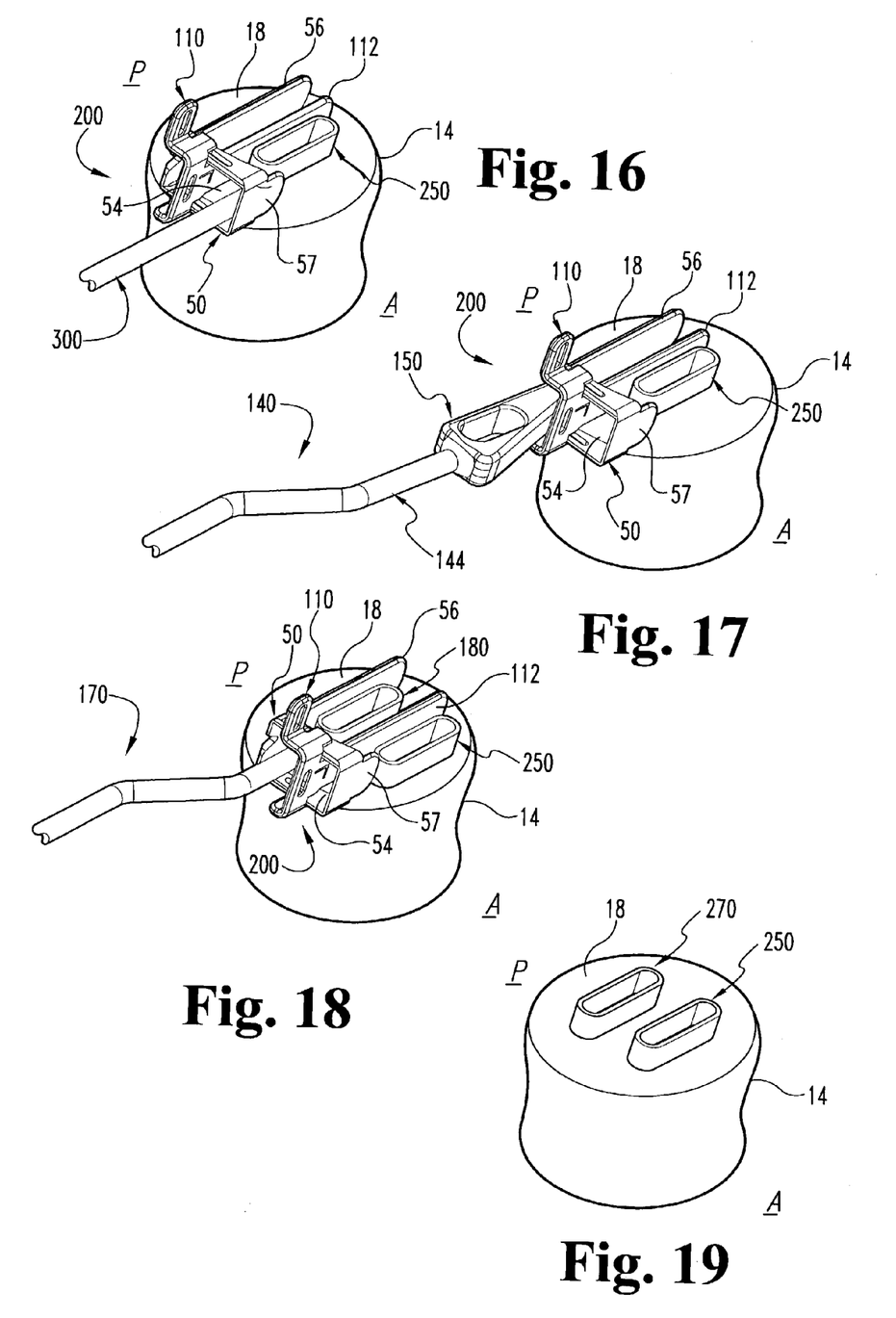
FIG. 16 is a perspective view of the assembly of FIG. 10 with an implant positioned in the spinal disc space along an anterior side of the partition member.
FIG. 17 is a perspective of the assembly of FIG. 10 with the wedge displacer instrument being inserted for positioning along the posterior side of the partition member.
FIG. 18 is a perspective of the assembly of FIG. 10 with the second displacer instrument positioned in the disc space along posterior side of the partition member.
FIG. 19 is a perspective view of the spinal disc space with medial-laterally oriented anterior and posterior implants positioned therein.

In FIG. 16 an implant 250 is removably attached or engaged to the distal end of an implant inserter 300. Implant 250 is positioned in disc space 18 between anterior extension 57 of housing 50 and central extension 112 of partition member 110. Implant inserter 300 is detached from implant 250, and, as shown in FIG. 17, wedge displacer instrument 140 is positioned so that leading end 152 of displacer wedge 150 is located between partition member 110 and posterior extension 56. A lever, if necessary, can be inserted between housing 50 and partition member 110 to provide an initial separation prior to insertion of displacer wedge 150. Wedge displacer instrument 140 is advanced distally until trailing end 154 is positioned between frame 50 and partition member 110, thereby moving partition member 110 and implant 250 anteriorly in disc space 18 and also anteriorly relative to housing 50.

Tapered leading end 152 of wedge displacer instrument 140 may not position central extension 112 and implant 250 anteriorly far enough so that implant 250 extends in a medial-lateral orientation in disc space 18, particularly at the distal end of central extension 112. In FIG. 18, second displacer instrument 170 is positioned into opening 54 between posterior extension 56 and partition member 110 and advanced distally to move at least the distal end of central extension 112 and thus implant 250 anteriorly in disc space 18 and to align implant 250 in a medial-lateral orientation. In its medial-lateral position, it is contemplated that implant 250 can be located in disc space 18 adjacent anterior extension 57. It is further contemplated that implant 250 can be displaced anteriorly so that is located in whole or in part anteriorly of anterior extension 57. Thus, the present invention provide positioning of the implant in the anterior portion of the spinal disc space while avoiding the major vessel and other anatomical structures along the anterior portion of the spinal column.

With implant 250 in a desired position in disc space 18, partition member 110 can be removed by, for example, attaching shaft assembly 126 thereto and withdrawing partition member 110 from disc space 18 and housing 50. In FIG. 17, a second implant 270 is positioned in disc space 18 through opening 54 of housing 50 in a medial-lateral orientation along a posterior side of first implant 250.

The instruments and methods of the present invention facilitate placement of implants 250, 270 in disc space 18 in a medial lateral orientation to provide bilateral support of the adjacent vertebrae 14, 16 in the anterior and posterior areas of disc space 18. It is further contemplated that only a single implant may be inserted in disc space 18. Bone graft, bone growth inducing material, and/or therapeutic agents can be positioned in, around or integrated into the one or more implants positioned in disc space 18. It is further contemplated that the one or more implants positioned in disc space 18 can be fusion devices, bone support devices, artificial disc devices, or other suitable device for implantation between vertebrae. The one or more implants can be provided with an outer surface structure to engage the vertebral endplates, and one or more chambers, cavities and/or recesses for receiving bone growth material. The one or more implants can also be flexible, or include one or more articulating components, to provide segmental motion between the adjacent vertebrae.

While the invention has been illustrated and described in detail in the drawings and foregoing description, the same is to be considered as illustrative and not restrictive in character. All changes, modifications and equivalents that come within the spirit of the invention as defined by the following claims are desired to be protected

What is claimed is:

1. A method for positioning an implant in a spinal disc space of a patient, comprising:
   accessing the spinal disc space between L4 and L5 vertebrae from an anterior lateral approach; and
   positioning a distractor in the spinal disc space with a shaft of the distractor oriented to extend along the anterior lateral approach, the shaft comprising a distal portion extending from the spinal disc space and a proximal portion remote from the disc space, said proximal portion including an offset relative to the distal portion so that said proximal portion is located anteriorly of said distal portion when said distractor is oriented in a medial-lateral direction in the disc space.

2. The method of claim 1, further comprising:
   guiding a housing along the distal portion of the distractor to a position adjacent the L4 and L5 vertebrae, the housing including a frame portion defining an opening therethrough for accessing the spinal disc space, said housing further including a posterior extension and an anterior extension each extending distally from said frame portion and positionable in the spinal disc space with said frame portion positioned adjacent the L4 and L5 vertebrae.

3. The method of claim 2, further comprising:
   positioning a partition member in the opening of the housing, the partition member including a central extension extending into the spinal disc space;
   moving the partition member relative to the housing to position the central extension adjacent the posterior extension.

4. The method of claim 3, further comprising inserting an implant into the spinal disc space through the opening of the housing between the central extension and the anterior extension.

5. The method of claim 4, further comprising moving the partition member anteriorly to move the implant anteriorly in the spinal disc space.

6. The method of claim 5, further comprising inserting a second implant into the spinal disc space through the opening of the housing and posterior of the anteriorly positioned implant.

7. The method of claim 6, further comprising removing the partition member from the housing before inserting the second implant.

8. The method of claim 5, wherein moving the partition member includes inserting a displacer head of a displacer instrument between the posterior extension and the central extension.

9. The method of claim 8, wherein inserting the displacer head includes inserting a wedge-shaped displacer head to provide an initial separation between the posterior extension and the central extension.

10. The method of claim 9, further comprising inserting a box-shaped displacer head between the posterior extension and the central extension after inserting the wedge-shaped displacer head.

11. A method for positioning a spinal implant in a spinal disc space of a patient, comprising:
    positioning a housing adjacent the spinal disc space between the L4 and L5 vertebrae in an anterior lateral approach;
    positioning a partition member through the housing into the spinal disc space;
    positioning an implant in the spinal disc space anteriorly of the partition member; and
    displacing the partition member anteriorly to move the implant anteriorly in the spinal disc space.

12. The method of claim 11, wherein displacing the partition member includes inserting a displacer head of a displacer instrument between a posterior wall of the housing and the partition member.

13. The method of claim 12, wherein inserting the displacer head includes inserting a wedge-shaped displacer head to provide an initial separation between the posterior wall and the partition member.

14. The method of claim 13, further comprising inserting a box-shaped displacer head between the posterior wall and the partition member after inserting the wedge-shaped displacer head.

15. The method of claim 12, wherein the posterior wall includes a posterior extension extending into the spinal disc space from the posterior wall of the housing, the housing further including an anterior extension opposite the posterior extension extending into the spinal disc space from an anterior wall of the housing.

16. The method of claim 15, wherein displacing the partition member anteriorly includes displacing the implant to a location at least partially anterior of the anterior extension.

17. The method of claim 11, further comprising inserting a second implant posteriorly of the anteriorly positioned implant.

18. The method of claim 17, wherein the first and second implant are medially-laterally oriented in the spinal disc space.

19. A method for positioning an implant in a spinal disc space of a patient, comprising:
    accessing the spinal disc space between L4 and L5 vertebrae from an anterior lateral approach;
    positioning a distractor in the spinal disc space with a shaft of the distractor oriented to extend along the anterior lateral approach, the shaft comprising a distal portion extending from the spinal disc space and a proximal portion offset relative to the distal portion;
    guiding a housing along the distal portion of the distractor to a position adjacent the L4 and L5 vertebrae, the housing including a frame portion defining an opening therethrough for accessing the spinal disc space, said housing further including a posterior extension and an anterior extension each extending distally from said frame portion and positionable in the spinal disc space with said frame portion positioned adjacent the L4 and L5 vertebrae;
    positioning a partition member in the opening of the housing, the partition member including a central extension extending into the spinal disc space;
    moving the partition member relative to the housing to position the central extension adjacent to posterior extension; and
    inserting an implant into the spinal disc space through the opening of the housing between the central extension and the anterior extension.

20. The method of claim 19, further comprising moving the partition member anteriorly to move the implant anteriorly in the spinal disc space.

21. The method of claim 20, further comprising inserting a second implant into the spinal disc space through the opening of the housing and posterior of the anteriorly positioned implant.

22. The method of claim 21, further comprising removing the partition member from the housing before inserting the second implant.

23. The method of claim 19, wherein moving the partition member includes inserting a displacer head of a displacer instrument between the posterior extension and the central extension.

24. The method of claim 23, wherein inserting the displacer head includes inserting a wedge-shaped displacer head to provide an initial separation between the posterior extension and the central extension.

25. The method of claim 24, further comprising inserting a box-shaped displacer head between the posterior extension and the central extension alter inserting the wedge-shaped displacer head.

26. A method for positioning an implant in a spinal disc space of a patient, comprising:
    accessing the spinal disc space between L4 and L5 vertebrae from an anterior lateral approach;
    positioning a distractor in the spinal disc space with a shaft of the distractor oriented to extend along the anterior lateral approach, the shaft comprising a distal portion extending from the spinal disc space and a proximal portion offset relative to the distal portion;
    guiding a housing along the distal portion of the distractor to a position adjacent the L4 and L5 vertebrae, the housing including a frame portion defining an opening therethrough for accessing the spinal disc space;
    positioning a partition member in the opening of the housing, the partition member including a central extension extending into the spinal disc space;
    inserting an implant into the spinal disc space through the opening of the housing adjacent the central extension; and
    moving the partition member anteriorly to move the implant anteriorly in the spinal disc space.

27. The method of claim 26, wherein said housing further includes a posterior extension and an anterior extension each extending distally from said frame portion and positionable in the spinal disc spare with said frame portion positioned adjacent the L4 and L5 vertebrae and said central extension is located between said anterior extension and said posterior extension.

28. The method of claim 27, wherein inserting the implant includes inserting the implant between said central extension and said anterior extension.

* * * * *